United States Patent

Zambounis

Patent Number: 5,349,062
Date of Patent: Sep. 20, 1994

[54] SUBSTITUTED NAPHTHO[1,8-DE:5,4-D'E']BIS[1,3]THIAZINES, PROCESS FOR THEIR PREPARATION AND THE USE THEREOF

[75] Inventor: John Zambounis, Murten, Switzerland

[73] Assignee: Ciba-Geigy Corporation, Ardsley, N.Y.

[21] Appl. No.: 83,814

[22] Filed: Jun. 28, 1993

[30] Foreign Application Priority Data

Jul. 2, 1992 [CH] Switzerland ............. 2087/92-3

[51] Int. Cl.⁵ .............. C07D 279/08; C07C 331/30
[52] U.S. Cl. .......................... 544/4; 544/14; 564/442; 558/17
[58] Field of Search ................. 544/14, 4

[56] References Cited

FOREIGN PATENT DOCUMENTS 2224746 11/1973 Fed. Rep. of Germany.
3814534 11/1989 Fed. Rep. of Germany.

OTHER PUBLICATIONS

K. Nakasuji et al, J. Am. Chem. Soc., vol. 109, No. 23, pp. 6970–6975, (1987).
K. Nakasuji et al, Synthetic Metals, vol. 42, No. 3, pp. 2529–2534, (1991).
Derw. Abst. 73-76041U/50 of DE 2,224,746 1973.
S. de Phys, C3, 44, pp. 1147–1152 (1983) V. Enkelmann.
S. Chem. Soc. pp. 221–226 (1951) S. Whitehurst.
Derwent Abst. 89-317307/44-of DE 3,814,534 1989.
Derwent Abst. CA 80(9):48022n of DE 2,224,746 1973.

Primary Examiner—Emily Bernhardt
Assistant Examiner—Matthew V. Grumbling
Attorney, Agent, or Firm—George R. Dohmann

[57] ABSTRACT

Compounds of formula I

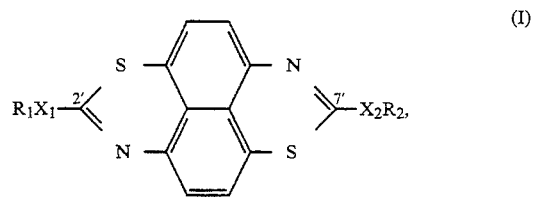

wherein
$X_1$ and $X_2$ are each independently of the other O, S or Se, and $R_1$ and $R_2$ are each independently of the other a monovalent radical of an aliphatic or aromatic hydrocarbon of 1 to 20 carbon atoms which is unsubstituted or substituted by $NH_2$, $C_1$–$C_6$alkyl, $C_1$–$C_6$alkoxy, phenyl or $C_3$–$C_8$cycloalkyl. The compounds of formula I are able to form electrically conductive charge transfer complexes.

15 Claims, No Drawings

SUBSTITUTED NAPHTHO[1,8-DE:5,4-D'E']BIS[1,3]THIAZINES, PROCESS FOR THEIR PREPARATION AND THE USE THEREOF

The present invention relates to naphtho[1,8-de:5,4-d'e']bis[1,3]thiazines which are substituted in the 2',7'-positions by organic thio, oxy or seleno radicals, to a process for their preparation and to the use thereof, and to 4,8-dibromo-1,5-diisothiocynatonaphthalene as intermediate.

Highly conductive charge transfer complexes of pyrene are described, inter alia, by V. Enkelmann in J. de Phys., C3, 44, pp. 1147–1152 (1983). These complexes are not storage-stable and decompose after a brief time. Mercaptopyrenes and their electrically conductive charge transfer complexes with inorganic anions are disclosed in DE-A-3 814 534. Tetracyclic chloro-bis-1,3-thiazine is disclosed in DE-A-2 224 746 as intermediate for the synthesis of plant protective agents and dyes.

Surprisingly, it has now been found that by means of a novel process it is possible to prepare naphtho[1,8-de:5,4-d'e']bis[1,3]thiazines which are substituted in the 2',7'-positions by organic thio, oxy or seleno radicals, and which form electrically conductive charge transfer complexes with inorganic anions. The charge transfer complexes normally crystallise in needle shape and have surprisingly high electrical conductivities.

In one of its aspects, the invention relates to compounds of formula I

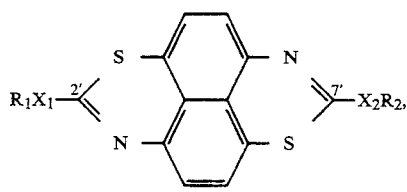

(I)

wherein
$X_1$ and $X_2$ are each independently of the other O, S or Se,
and $R_1$ and $R_2$ are each independently of the other a monovalent radical of an aliphatic or aromatic hydrocarbon of 1 to 20 carbon atoms which is unsubstituted or substituted by $NH_2$, $C_1$–$C_6$alkyl, $C_1$–$C_6$alkoxy, phenyl or $C_3$–$C_8$cycloalkyl. $R_1$ and $R_2$ are preferably identical radicals.

The hydrocarbon radicals preferably contain 1 to 18, more particularly 1 to 12 and, most preferably, 1 to 8, carbon atoms.

Suitable aliphatic hydrocarbons $R_1$ and $R_2$ are typically $C_1$–$C_{18}$alkyl, preferably $C_7$–$C_{12}$alkyl, most preferably $C_1$–$C_6$alkyl, $C_3$–$C_8$cycloalkyl or, preferably, $C_4$–$C_6$cycloalkyl, $C_7$–$C_{12}$aralkyl and, most preferably, $C_7$–$C_{12}$phenylalkyl. Typical examples are ethyl, methyl, propyl and linear or branched dodecyl, undecyl, decyl, nonyl, octyl, heptyl, hexyl, pentyl and butyl. Typical examples of cycloalkyl are cyclopropyl, cyclobutyl, cyclopentyl, cyclohexyl, cycloheptyl and cyclooctyl. Typical examples of aralkyl are benzyl and phenylethyl.

Suitable aromatic hydrocarbon radicals $R_1$ and $R_2$ are typically $C_6$–$C_{18}$aryl and, preferably, $C_6$–$C_{12}$aryl. Preferred examples are phenyl and naphthyl.

In a preferred embodiment, $R_1$ and $R_2$ are $C_1$–$C_{18}$alkyl, preferably $C_1$–$C_{12}$alkyl, unsubstituted or substituted as defined above, $C_5$–$C_6$cycloalkyl, phenyl or benzyl.

$X_1$ and $X_2$ preferably have the same meaning. Preferably $X_1$ and/or $X_2$ are O or S. Most preferably, $X_1$ and $X_2$ are identical and are O or S.

Typical examples of cycloalkyl substituents are cyclopropyl, cyclopentyl, cyclohexyl, cycloheptyl and cyclooctyl. Preferred cycloalkyl radicals are cyclopentyl and cyclohexyl.

Exemplary alkyl substituents which preferably contain 1 to 4 carbon atoms are methyl, ethyl, n- and isopropyl, and n-, iso- and tert-butyl.

Typical examples of alkoxy substituents $R_1$ and $R_2$ which preferably contain 1 to 4 carbon atoms are methoxy, ethoxy, n-propoxy and tert-butoxy.

A preferred subgroup of substituents $R_1$ and $R_2$ comprises methyl, ethyl, methoxy and ethoxy.

Preferably $R_1$ and $R_2$ are methyl, ethyl, n-propyl, n-butyl, benzyl and phenyl.

Representative examples of compounds of formula I are 2',7'-bis(methylthio)naphtho-[1,8-de:5,4-d'e']-bis[1,3]thiazine, 2',7'-bis(methoxy)naphtho[1,8-de:5,4-d'e']bis[1,3]thiazine, 2'-methylthio-7'-ethoxynaphtho[1,8-de:5,4-d'e']bis[1,3]thiazine, and 2'-n-butylthio-7'-methylionaphtho[1,8-de:5,4-d'e']bis[1,3]thiazine.

The compounds of formula I can be prepared in simple manner and by a novel process.

In another of its aspects, the invention relates to a process for the preparation of compounds of formula I, which comprises i) thiophosgenating 4,8-dibromo-1,5-diaminonaphthalene of formula II, which may be in salt form,

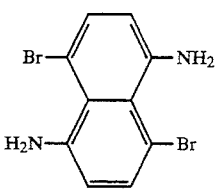

(II)

in the presence of an inert solvent and $Na_2CO_3$, to 4,8-dibromo-1,5-diisothiocyanatonaphthalene of formula III

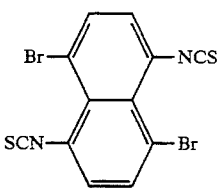

(III)

ii) converting the 4,8-dibromo-1,5-diisothiocyanatonaphthalene of formula III, in the presence of a solvent, either by reacting 2 equivalents of a monovalent metal salt or ammonium salt $R_1X_1^-M^+$ or of an alkaline earth metal salt $(R_1X_1^-)_2E^{2+}$, into a compound of formula Ia

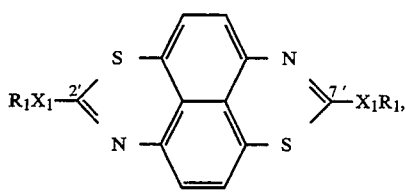

wherein M+ is a monovalent metal cation or an ammonium cation $R_3R_4R_5R_6N^+$, and $R_3$, $R_4$, $R_5$ and $R_6$ are each independently of one another H or $C_1$–$C_4$alkyl, and $E^{2+}$ is an alkaline earth metal cation, or stepwise by first reacting 4,8-dibromo-1,5-diisothiocyanatonaphthalene of formula III with 1 equivalent of a monovalent metal salt or ammonium salt $R_1X_1^-M^+$ or of an alkaline earth metal salt $(R_1X_1^-)_2E^{2+}$, and then converting the reaction product with 1 equivalent of another monovalent metal salt or ammonium salt $R_2X_2^-M^+$, or of another alkaline earth metal salt $(R_2X_2^-)_2E^{2+}$, into a compound of formula I

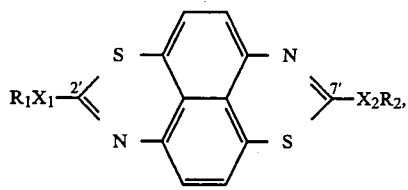

wherein $R_1$, $R_2$, $X_1$ and $X_2$ are as previously defined.

Representative examples of M+ are Li+, Na+, K+, Cu+, Tl+, NH4+, (CH3)3NH+ and (C2H5)3NH+. Representative examples of $E^{2+}$ are $Mg^{2+}$, $Ca^{2+}$ and $Sr^{2+}$. Cu+ is commercially available as C6H5SCu. Most preferably M+ is Na+, K+, NH4+, (CH3)3NH+ and (C2H5)3NH+. In another preferred embodiment, M+ is an alkali metal cation.

The steps of the entire reaction can be carried out in the temperature range from 5° to 80° C., preferably from 15° to 60° C.

Suitable solvents for both reaction steps are conveniently polar and aprotic solvents and include typically the following solvents: sulfones; sulfoxides; N,N'-tetrasubstituted ureas; N-alkylated lactams or N-dialkylated acid amides; ethers; unsubstituted or halogenated aliphatic, cycloaliphatic or aromatic hydrocarbons; carboxylates and lactones; nitriles.

Typical examples are of such solvents are:
Sulfones: dimethyl sulfone, diethyl sulfone.
Sulfoxides: dimethyl sulfoxide, diethyl sulfoxide.
N,N-Tetra-substituted ureas: N-Methylethyl-N'-methylethylurea, tetramethylurea.
N-Alkylated lactams: N-methylpyrrolidone, N-ethylpyrrolidone.
N-Dialkylated acid amides: N-dimethylformamide, N-dimethylacetamide.
Ethers: diethylene glycol dimethyl ether, diethylene glycol diethyl ether, tetrahydrofuran.
Aliphatic hydrocarbons: dichloromethane, hexane, chloroform, trichloroethane, tetrachloroethane.
Aromatic hydrocarbons: chlorobenzene, dichlorobenzene.
Carboxylates: methyl acetate, ethyl acetate.

Nitriles: benzonitrile, phenyl acetonitrile, acetonitrile.

Preferred solvents are dichloromethane, tetrahydrofuran and dimethyl formamide.

The novel process, especially the second step, is expediently carried out under an inert atmosphere, conveniently in a rare gas such as argon or under nitrogen.

The product of each step can be isolated in per se known manner, typically by decantation, filtration or distillation. Afterwards the products can be purified by conventional methods such as crystallisation or chromatographic methods.

The preparation of the starting 4,8-dibromo-1,5-diaminonaphthalene of formula II is known per se and described by J. S. Whitehurst in J. Chem. Soc., pp. 221–226 (1951). 4,8-Dibromo-1,5-ditoluene-p-sulfonamidonaphthalene is dissolved in concentrated acid, conveniently in $H_2SO_4$, and left to stand for 24 hours, excluding light. For reasons of stability, the compound of formula II is preferably isolated as $HSO_4^-$ salt.

The intramolceular cyclisation in process step (ii) is achieved under surprisingly mild reaction conditions and the compounds of the invention are obtained in high yield and purity.

In yet another of its aspects, the invention relates to the compound 4,8-dibromo-1,5-diisothiocyanatonaphthalene of formula III

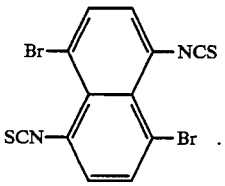

The compounds of formula I can be convened electrolytically or chemically into cations by reaction with an oxidising agent and form electrically conductive charge transfer complexes with different anions.

The novel compounds of formula I form charge transfer complexes of stoichiometric or non-stoichiometric composition with inorganic anions.

In yet another of its aspects, the invention relates to charge transfer complexes of formula IV $$Z_xA_y \qquad (IV),$$

wherein Z is the radical cation of a compound of formula I and A is the anion of an inorganic acid, and $1 \leq x/y \leq 3$. The stoiichiometry (ratio of the cation of the compounds of formula I and counter-anion) is preferably from 1:1 and 2:1.

The inorganic acids are preferably monobasic acids, typically mineral acids, oxyacids and complex acids.

Suitable anions are typically: F−, Cl−, Br−, I−, CN−, OCN−, SCN−, SeCN−, N3−, I3−, I2Br−, IBr2−, BrICl−, Br3−, ICl2−, CuCl2−, CuBr2−, AgCl2−, AgBr2−, AgI2−, Ag(CN)2−, AuCl2−, AuBr2−, AuI2−, Au(CN)2−, NO3−, C(CN)3−, ClO4−, BrO4−, IO4−, ReO4−, FSO3−, PO2F2−, BF4−, InBr4−, InI4−, TlBr4−, TlI4−, FeCl4−, AuCl4−, AuBr4−, ICl4−, SiF5−, TeF5−, PF6−, AsF6−, SbF6−, SbCl6−, NbF6− and TaF6−.

Preferred anions are I3−, IBr2−, Br3−, CuCl2− and PF6−. IBr2− is especially preferred.

The charge transfer complex salts can be prepared electrolytically or chemically. In the electrolytic method the procedure may be as follows: the compound of formula I is filled into the anode region of an electrolytic cell in which there are present a conductive electrolyte with a salt of the inorganic anion, for example a tetraalkylammonium salt such as tetrabutylammonium hexafluorophosphate, and a solvent, e.g. dichloromethane. Electrolysis is carried out at a current strength of c. 0.5 μA and, after some time, typically 1 or 2 days, the crystals can be removed from the electrode and purified.

In the chemical method, the procedure is as follows: a solution or a hot solution of the compound of formula I in a solvent, e.g. toluene, is mixed with a solution of an oxidising agent, typically halogen, $CuCl_2$, $FeCl_3$. After the reaction solution has cooled, the precipitated crystals are isolated by filtration and purified.

The novel charge transfer complexes have excellent electrical conductivities and can be used as electrical conductors.

The invention further relates to the use of the charge transfer complexes of formula IV as electrical conductors.

The charge transfer complexes of formula IV can typically be used for coating surfaces (antistatic finish), or they can be blended into plastic materials as electrically conductive fillers. It is also possible to coat substrates with mono- or multimolecular layers of compounds of formula I by the Langmuir-Blodgett technique and to dope these layers with e.g. halogens. Such substrates coated with thin electrically conductive layers are suitable base materials for the preparation of sensors.

The following Examples illustrate the invention in more detail.

A. Preparation of the novel compounds of formula I

EXAMPLE A1 a) Preparation of 4,8-dibromo-1,5-diaminonaphthalene 15 g (0.024 mol) of 4,8-dibromo-1,5-ditoluene-p-sulfonamidonaphthalene (J. S. Whitehurst, J. Chem. Soc., 221–226 (1951)) are dissolved in 75 ml of concentrated $H_2SO_4$ and the solution is left to stand for 24 h, excluding light. The solution is then poured on to 450 g of ice, whereupon a violet solution forms from which the product precipitates as $HSO_4$ salt after a few minutes. The precipitate is isolated by suction filtration and the filter cake is squeezed out to give a pale beige-violet crude product that is further processed immediately.

b) Preparation of 4,8-dibromo-1,5-diisothiocyanatonaphthalene

The crude 4,8-dibromo-1,5-diaminonaphthalene obtained in a) in the form of the $HSO_4$ salt is suspended in 150 ml of $H_2O$ and the suspension is underlaid with 150 ml of $CH_2Cl_2$. With stirring, 18 g of $Na_2CO_3$ are added in increments. A solution of 6.3 g (0.054 mol) of thiophosgene in 30 ml of $CH_2Cl_2$ is then added dropwise to this emulsion at room temperature (RT). After stirring for 2 h at RT the reaction is complete. The product is extracted with 600 ml of water and 600 ml of $CH_2Cl_2$. The aqueous phase is extracted once more with 200 ml of $CH_2Cl_2$, and the organic phases are dried with $MgSO_4$, filtered and concentrated by evaporation under vacuum. The residue (7.7 g) is dissolved warm in 600 ml of $CH_2Cl_2$ and, after cooling to RT, the solution is filtered over 500 g of silica gel and then over activated carbon. The filtrate is concentrated under vacuum to a volume of 300 ml and the precipitated crystals are filtered with suction. Yield: 3.8 g (40%), melting point (m.p.): 202°–204° C. The crystalline product is dissolved hot in 500 ml of $CH_2Cl_2$, the solution is concentrated to 200 ml and then crystallised. After cooling with ice and suction filtration, 2.7 g of the title compound with a melting point of 213.5°–214° C. are obtained. MS (m/e): 400 (M+, 100%), IR ($v_{max}$, KBr): 2095 cm$^{-1}$ (N=C=S). A further 0.35 g of tile compound can be isolated from the mother liquor, m.p.: 207°–209° C. (owing to the lower quality).

c) Preparation of 2′,7′-bis(methylthio)naphtho[1,8-de:5,4-d′e′]bis[1,3]thiazine (Methode "A")

100 mg (1.5 mmol) of sodium methane thiolate are added in increments at 50° C. under argon to a stirred suspension of 200 mg (0.5 mmol) of 4,8-dibromo-1,5-diisothiocyanatonaphthalene in 4 ml of absolute dimethyl formamide. The educt thereupon dissolves, the reaction mixture first turns yellowish and then orange, and the product precipitates from the warm solution. The batch is stirred for 15 minutes at 50° C., then cooled and filtered with suction, and the filter product is washed with water, ethanol and diethyl ether. The crude product is dissolved in 80 ml of hot $CH_2Cl_2$ and the solution is chromatographed over 800 g of silica gel with $CH_2Cl_2$/hexane (1:1). The main zone yields 108 mg (64.6%) of orange crystals with a melting point of 243.5°–244° C. MS (m/e): 334 (M+, 100%), IR ($v_{max}$, KBr): 1558 cm$^{-1}$ (C=C).

EXAMPLE A2

Preparation of 2′,7′-bis(phenylthio)naphtho[1,8-de:5,4-d′e′]bis[1,3]thiazine (Method "B")

A solution of 135 mg (1.2 mmol) of thiophenol in 4 ml of dimethyl formamide is added dropwise at 50° C. under argon to a stirred suspension of 200 mg (0.5 mmol) of 4,8-dibromo-1,5-diisocyanatonaphthalene and 130 mg (1.2 mmol) of triethylamine in 4 ml of dimethyl formamide. The educt thereupon dissolves, the reaction mixture turns yellowish and then dark orange, and the product precipitates from the warm solution. After 15 h at 50° C., the suspension is cooled, filtered with suction, and the filter product is washed with dimethyl formamide, water and diethyl ether. The crude product is recrystallised from 50 ml of toluene, giving 180 mg of orange crystals, m.p.: 299.4° C. MS (m/e): 458 (M+, 100%), IR ($v_{max}$, KBr): 1558 cm$^{-1}$ (C=C); Yield 87.3%.

EXAMPLE A3

Preparation of 2′-n-butylthio-4-bromo-5-isothiocyanato-naphtho[1,8-de][1,3]thiazine 110 mg (1.2 mmol) of n-butylmercaptan (97%) are added at RT to a suspension of 400 mg (1 mmol) of 4,8-dibromo-1,5-diisothiocyanatonaphthalene and 130 mg (1.2 mmol) of triethylamine in 15 ml absolute tetrahydrofuran, and the mixture is heated to reflux. In the course of heating, a homogeneous reaction mixture initially forms. After 5 minutes, $(C_2H_5)_3N$ HBr precipitates from the yellow-orange solution. The batch is heated for 4 h under reflux, then concentrated to dryness under vacuum. The residue is taken up in benzene/hexane (1:2) and chromatographed with this mixture over 50 g of silica gel. The lemon-yellow main zone affords the title compound in a yield of 213 mg (51)% of lemon-yellow crystals, m.p.: 93.5°–94° C., MS (m/e): 410 (M+, 100%), IR ($\nu_{max}$, KBr): 2110 (N=C=S), 1550 (C=C) cm$^{-1}$.

EXAMPLES A4–7

The following compounds are prepared in accordance with the general procedure described in Example A3 and can be used for the preparation of unsymmetric compounds of formula I.

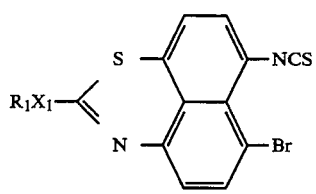

| X$_1$ | R$_1$ | m.p. (°C.) | Method |
|---|---|---|---|
| S | —(CH$_2$)$_3$CH$_3$ | 93.5–94 | B |
| S | —CH$_3$ | 172.5 | A |
| O | —CH$_3$ | 231–232 | A |
| S | —(CH$_2$)$_{11}$CH$_3$ | 84–84.5 | B |

EXAMPLE A8

Preparation of 2'-n-butylthio-7'-methylthionaphtho[1,8-de:5,4-d'e']-bis[1,3]thiazine 23 mg (0.33 mmol) of CH$_3$SNa are added dropwise at 50° C. under argon to 102 mg (0.25 mmol) of the title compound according to Example A3 in 3 ml of dimethyl formamide. The solution turns red immediately. After 2 h at 60° C., the suspension is cooled, diluted with 10 ml of water and extracted with CH$_2$Cl$_2$. The extraction solution is washed with water, dried over MgSO$_4$ and concentrated under vacuum. The residue is chromatographed over 75 g of silica gel (benzene/hexane, 1:2). The second orange-red zone contains orange crystals of the title compound. Yield: 31 mg (33%), m.p.: 121.5°–122° C., MS (m/e): 376 (M+, 100%), IR ($\nu_{max}$, KBr): 1556 cm$^{-1}$ (C=C).

EXAMPLES A9–A20

The following compounds are prepared in accordance with the general procedure described in Example A8.

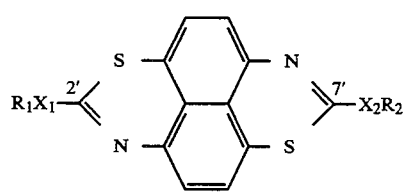

| X$_1$ | X$_2$ | R$_1$ | R$_2$ | m.p. (°C.) | Method |
|---|---|---|---|---|---|
| S | S | —(CH$_2$)$_3$CH$_3$ | =R$_1$ | 101–101,5 | B |
| S | S | —CH$_3$ | =R$_1$ | 243.5–244 | A |
| S | S | —C$_6$H$_5$ | =R$_1$ | 299.4 | B |
| O | O | —(CH$_2$)$_3$CH$_3$ | =R$_1$ | 145.5–146.5 | A |
| O | O | —CH$_3$ | =R$_1$ | 278–279 | A |
| O | O | —C$_6$H$_5$ | =R$_1$ | 264–265 | A |

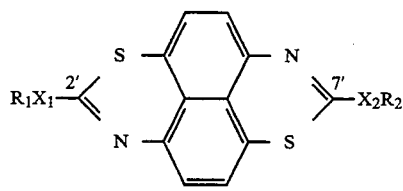

| X$_1$ | X$_2$ | R$_1$ | R$_2$ | m.p. (°C.) | Method |
|---|---|---|---|---|---|
| S | S | —(CH$_2$)$_3$CH$_3$ | —CH$_3$ | 121.5–122 | B or A |
| S | O | —(CH$_2$)$_3$CH$_3$ | —CH$_3$ | 76–77 | B or A |
| O | S | —CH$_3$ | —CH$_3$ | 230 | A or A |
| Se | Se | —CH$_3$ | —CH$_3$ | 232.6–233 | A |
| S | S | —(CH$_2$)$_{11}$CH$_3$ | =R$_1$ | 96.7–97 | B |
| S | S | —CH$_3$ | —(CH$_2$)$_{11}$CH$_3$ | 98.5–99 | A or B |

=R$_1$ denotes the same meaning as R$_1$

B. Preparation of charge transfer complex salts

Preparation of [2',7'-bis(methylthio)naphtho[1,8-de:5,4-d'e']bis[1,3]-thiazino]$_2$hexafluorophosphate 5 mg (0.015 mmol) of 2',7'-bis(methylthio)naphtho[1,8-de:5,4-d'e']bis[1,3]thiazine are filled into the anode region of an electrolytic cell of 6 ml volume. 15 mg (0.04 mmol) of tetrabutylammonium-PF$_6$ are used as conductive electrode and are also filled into the cell under argon. 3 ml of dichloromethane are used as solvent. Then a current of 0.5 μA is applied (Pt wire electrodes 1×10 mm). After two days, thick black needles of the title compound are obtained. The electrical conductivity of this complex as single crystal is $\sigma_{RT}$=25 S/cm (measured by the four-point method). The stoichiometry is confirmed by X-ray structural analysis.

EXAMPLE B2

Preparation of [2',7'-bis(methylthio)naphtho[1,8-de;5,4-d'e']bis[1,3]-thiazino](I$_3$)$_{0,46}$ A solution of 19 mg (0.075 mmol) of iodine in 1 ml of toluene is added to a solution of 33.4 mg (0.1 mmol) of 2',7'-bis(methylthio)naphtho[1,8-de:5,4-d'e']bis[1,3]thiazine in 3 ml of hot toluene. After cooling the solution, the precipitated golden crystals are isolated, washed with a small amount of toluene and dried in the air. Yield: 48 mg (90%), m.p.: 205° C. The conductivity of a single crystal is 150 S/cm (measured by the four-point method). The structure is determined by elemental analysis.

What is claimed is:

1. A compound of formula I

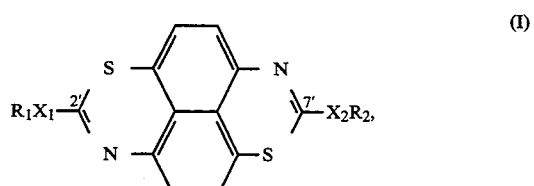

wherein

X$_1$ and X$_2$ are each independently of the other O, S or Se, and R$_1$ and R$_2$ are each independently of the other a monovalent radical of an aliphatic or aromatic hydrocarbon, wherein the aliphatic hydrocarbon radicals are selected from the group consisting of $C_1$-$C_{18}$alkyl, $C_3$-$C_8$cycloalkyl and $C_7$-$C_{12}$aralkyl, which aliphatic hydrocarbon radicals are unsubstituted or substituted by $NH_2$, $C_1$-$C_6$alkoxy or phenyl, and the aromatic hydrocarbon radicals are selected from the group consisting of $C_6$-$C_{18}$aryl, which aromatic hydrocarbon radicals are substituted by $NH_2$, $C_1$-$C_6$alkyl, $C_1$-$C_6$alkoxy or $C_3$-$C_8$cycloalkyl.

2. A compound according to claim 1, wherein $X_1$ and $X_2$ are identical.

3. A compound of formula I according to claim 2, wherein $X_1$ and $X_2$ are S.

4. A compound of formula I according to claim 2, wherein $X_1$ and $X_2$ are O.

5. A charge transfer complex of formula IV $$Z_xA_y \qquad (IV)$$

wherein Z is the radical cation of a compound of formula I

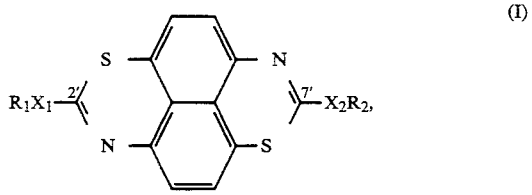
(I)

wherein
$X_1$ and $X_2$ are each independently of the other O, S or Se,
and $R_1$ and $R_2$ are each independently of the other a monovalent radical of an aliphatic or aromatic hydrocarbon, wherein the aliphatic hydrocarbon radicals are selected from the group consisting of $C_1$-$C_{18}$alkyl, $C_3$-$C_8$cycloalkyl and $C_7$-$C_{12}$aralkyl, which aliphatic hydrocarbon radicals are unsubstituted or substituted by $NH_2$, $C_1$-$C_6$alkoxy or phenyl, and the aromatic hydrocarbon radicals are selected from the group consisting of $C_6$-$C_{18}$aryl, which aromatic hydrocarbon radicals are substituted by $NH_2$, $C_1$-$C_6$alkyl, $C_1$-$C_6$alkoxy or $C_3$-$C_8$cycloalkyl, and A is the anion of an inorganic acid, and $1 \leq x/y \leq 3$.

6. A compound of formula I according to claim 1, wherein the aliphatic hydrocarbon radicals are selected from the group consisting of $C_1$-$C_{12}$alkyl, $C_4$-$C_6$cycloalkyl and $C_7$-$C_{12}$aralkyl, and the aromatic hydrocarbon radicals are $C_6$-$C_{12}$aryl.

7. A compound of formula I according to claim 1, wherein $R_1$ and $R_2$ are $C_1$-$C_{18}$alkyl, unsubstituted or substituted as defined in claim 1, $C_5$-$C_6$cycloalkyl, phenyl or benzyl.

8. A compound of formula I according to claim 1, wherein $R_1$ and $R_2$ are $C_1$-$C_{12}$alkyl, phenyl or benzyl.

9. A compound of formula I according to claim 1, which is 2',7'-bis(methylthio)naphtho[1,8-de:5,4-d'e']-bis[1,3]thiazine.

10. A compound of formula I according to claim 1, which is 2',7'-bis(methoxy)naphtho[1,8-de:5,4-d'e']-bis[1,3]thiazine.

11. A compound of formula I according to claim 1, which is 2'-methylthio-7'-ethoxynaphtho[1,8-de:5,4-d'e']bis[1,3]thiazine.

12. A compound of formula I according to claim 1, which is 2'-n-butylthioethylthionaphtho[1,8-de:5,4-d'e']bis[1,3]thiazine.

13. A charge transfer complex of formula IV as claimed in claim 5, wherein the anion A is selected from the group consisting of $F^-$, $Cl^-$, $Br^-$, $I^-$, $CN^-$, $OCN^-$, $SCN^-$, $SeCN^-$, $N_3^-$, $I_3^-$, $I_2Br^-$, $IBr_2^-$, $BrICl^-$, $Br_3^-$, $ICl_2^-$, $CuCl_2^-$, $CuBr_2^-$, $AgCl_2^-$, $AgBr_2^-$, $AgI_2^-$, $Ag(CN)_2^-$, $AuCl_2^-$, $AuBr_2^-$, $AuI_2^-$, $Au(CN)_2^-$, $NO_3^-$, $C(CN)_3^-$, $ClO_4^-$, $BrO_4^-$, $IO_4^-$, $ReO_4^-$, $FSO_3^-$, $PO_2F_2^-$, $BF_4^-$, $InBr_4^-$, $InI_4^-$, $TlBr_4^-$, $TlI_4^-$, $FeCl_4^-$, $AuCl_4^-$, $AuBr_4^-$, $ICl_4^-$, $SiF_5^-$, $TeF_5^-$, $PF_6^-$, $AsF_6^-$, $SbF_6^-$, $SbCl_6^-$, $NbF_6^-$ and $TaF_6^-$.

14. A charge transfer complex as claimed in claim 5, which is [2',7'-bis(methylthio)naphtho[1,8-de:5,4-d'e']-bis[1,3]thiazino]$_2$hexafluorophosphate.

15. A charge transfer complex as claimed in claim 5, which is [2',7'-bis(methylthio)naphtho[1,8-de:5,4-d'e']-bis[1,3]thiazino]$(I_3)_{0.46}$.

* * * * *